United States Patent [19]

Du Bois

[11] Patent Number: 4,613,845
[45] Date of Patent: Sep. 23, 1986

[54] APPARATUS FOR PREVENTING OPERATION OF MACHINERY BY ONE WHO IS INTOXICATED

[76] Inventor: Donald E. Du Bois, Rte. 28, Shokan, N.Y. 12481

[21] Appl. No.: 478,357

[22] Filed: Mar. 24, 1983

[51] Int. Cl.$^4$ .................. B60Q 1/00; G08B 23/00
[52] U.S. Cl. .................. 340/52 R; 340/576; 180/272
[58] Field of Search .......... 340/576, 53, 561, 562, 340/506, 507, 521, 522; 180/272; 128/716, 719

[56] References Cited

U.S. PATENT DOCUMENTS

| | | | |
|---|---|---|---|
| 3,103,655 | 9/1963 | Jones | 340/561 |
| 3,815,087 | 6/1974 | Hirano | 340/53 |
| 3,831,707 | 8/1974 | Takeuchi | 340/576 |
| 3,855,573 | 12/1974 | Honda et al. | 180/272 |
| 4,030,037 | 6/1977 | Tanaka et al. | 340/520 |
| 4,103,293 | 7/1978 | La Forge, Jr. | 340/522 |
| 4,117,467 | 9/1978 | San | 340/506 |

*Primary Examiner*—John W. Caldwell, Sr.
*Assistant Examiner*—Tyrone Queen
*Attorney, Agent, or Firm*—John Maier, III

[57] ABSTRACT

An apparatus for preventing the operation of machinery such as a motor vehicle by an operator who is intoxicated, such apparatus including an alcohol sensor and a proximity sensor located in the control area of the machinery.

2 Claims, 3 Drawing Figures

APPARATUS FOR PREVENTING OPERATION OF MACHINERY BY ONE WHO IS INTOXICATED

BACKGROUND OF THE INVENTION

1. Field of the Invention

The present invention relates to an apparatus for preventing the operation of machinery by an intoxicated operator. More particularly, the present invention is directed to an apparatus utilizing an alcohol sensor for use on machinery such as the motor vehicle to prevent starting of the machinery in the presence of alcohol and a proximity sensor to prevent blocking of the alcohol sensor. Accordingly, the general objects of the present invention are to provide a novel and improved apparatus of such character.

2. Description of the Prior Art.

Increasingly, the problem of intoxicated drivers has become a national crisis. The major approach at the current time to the prevention of intoxicated drivers is through law enforcement. Unfortunately, it is a recognized fact that only a small portion of the intoxicated drivers on the road are actually apprehended. Devices for automobiles have been proposed to prevent an intoxicated driver from starting an automobile such as the sequential operation of push buttons as a condition precedent in order for the motor vehicle to be capable of being started. However, the unpopularity of such a device with sober drivers and the ability to have another person who is sober start the vehicle for an intoxicated operator has limited the desirability of such a device. Automobiles are one of the most important areas to use such a device but it is also applicable to many types of machinery including stationary machinery used in a factory such as a crane and in particular to all types of propelled equipment as for example subway trains and even boats.

The novel features which are considered as characteristic of the invention are set forth with particularity in the appending claims. The invention, itself, however, as to its construction and obvious advantages, will best be understood from the following description of the specific embodiment when read with the accompanying drawings.

SUMMARY OF THE INVENTION

The present invention overcomes the disadvantages of the prior art and in so doing provides a reliable, durable and easily-used apparatus for preventing the operation of machinery such as a motor vehicle by an intoxicated operator. Such an apparatus is preferably located on machinery, such as a motor vehicle, at the console where the operator is situated when operating the machinery. The machinery so equipped would have an electrical power source and be electrically actuated. An alcohol sensor is preferably located in the steering wheel or control area to determine the state of intoxication of the operator. The alcohol sensor is adapted to transmit a signal when activated by the presence of alcohol at or above a specified level. The alcohol sensor causes the circuit which electrically actuates the machinery to open when alcohol is present.

DESCRIPTION OF THE DRAWINGS

The present invention may be better undertood and its numerous advantages will become apparent to those skilled in the art by reference to the accompanying drawings wherein like reference numerals refer to like elements in the various figures in which.

DETAILED DESCRIPTION OF THE INVENTION

Figure 1:
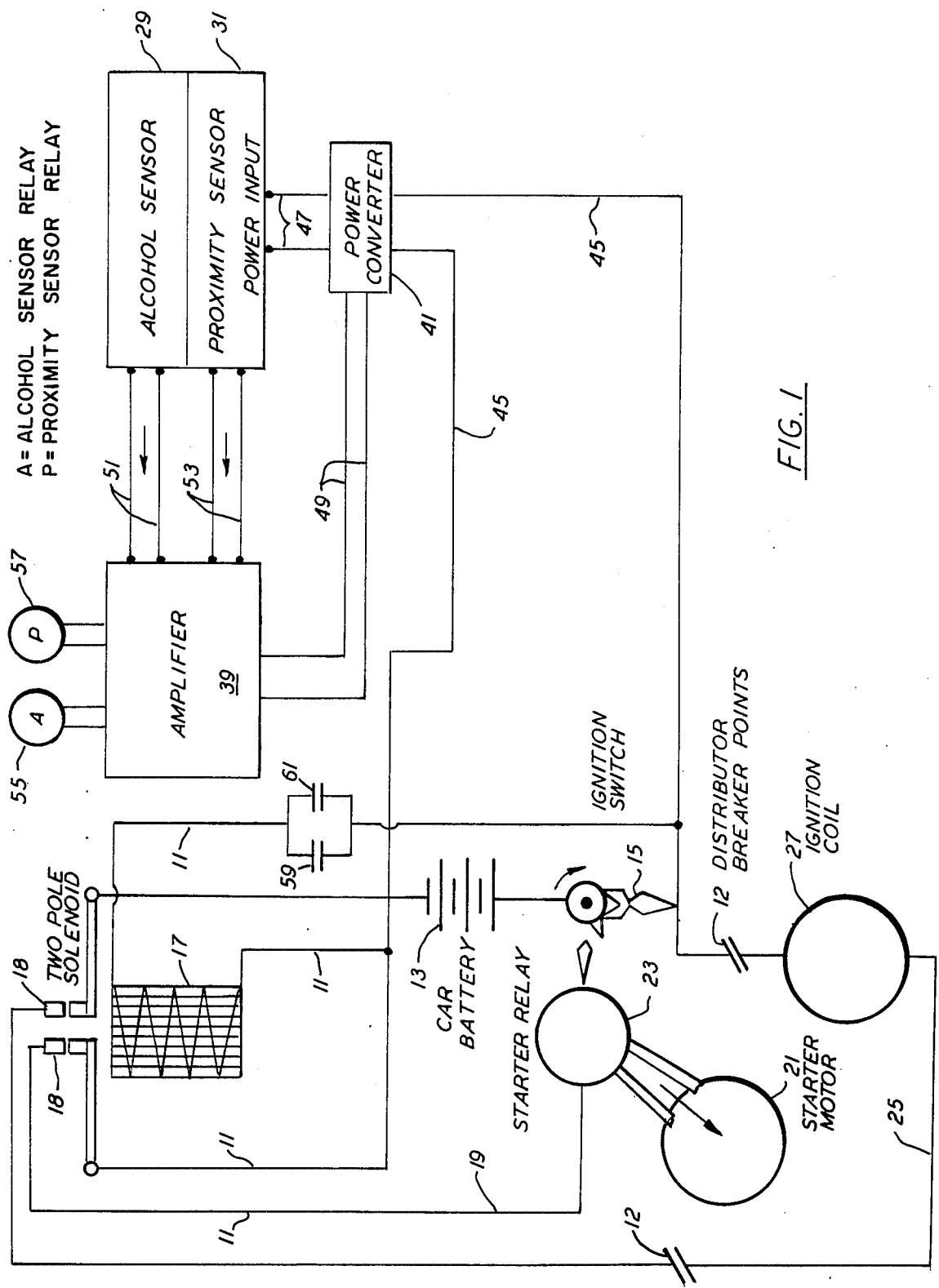
FIG. 1 is a schematic diagram of the circuitry showing the alcohol and proximity sensors and circuitry in combination with the prior art parts of the machinery, in particular a motor vehicle.

As best seen in FIG. 1, the apparatus according to this invention is shown as used in a motor vehicle application. It is to be understood, however, that this invention can be utilized with any type of machinery particularly where the machinery is started by the closing of an electrical circuit. Such a circuit 11 usually contains at least one set of distributor break points 12. In an automobile, as is well known, a starting circuit 11 is provided including a battery 13 and an ignition switch 15 which closes the starting circuit 11. A two-pole solenoid 17 which is normally deactivated is added and its contacts 18 are normally closed. Upon closing the ignition switch 15 two separate branches of the starting circuit 11 are energized through the normally closed contacts 18. One of the branches 19 of the starting circuit 11 activates a starter motor 21 through a starter relay 23 to turn over an internal combustion engine (not shown) and the other branch 25 of the starting circuit 11 provides electrical power to the ignition equipment 27 of the internal combustion engine (not shown) namely the spark plugs, ignition coil or electronic ignition should the motor vehicle be so equipped. The ignition switch 15 is of the usual two-step variety in which the ignition equipment 27 is first energized and then the starter motor 21 is energized.

Figure 2:
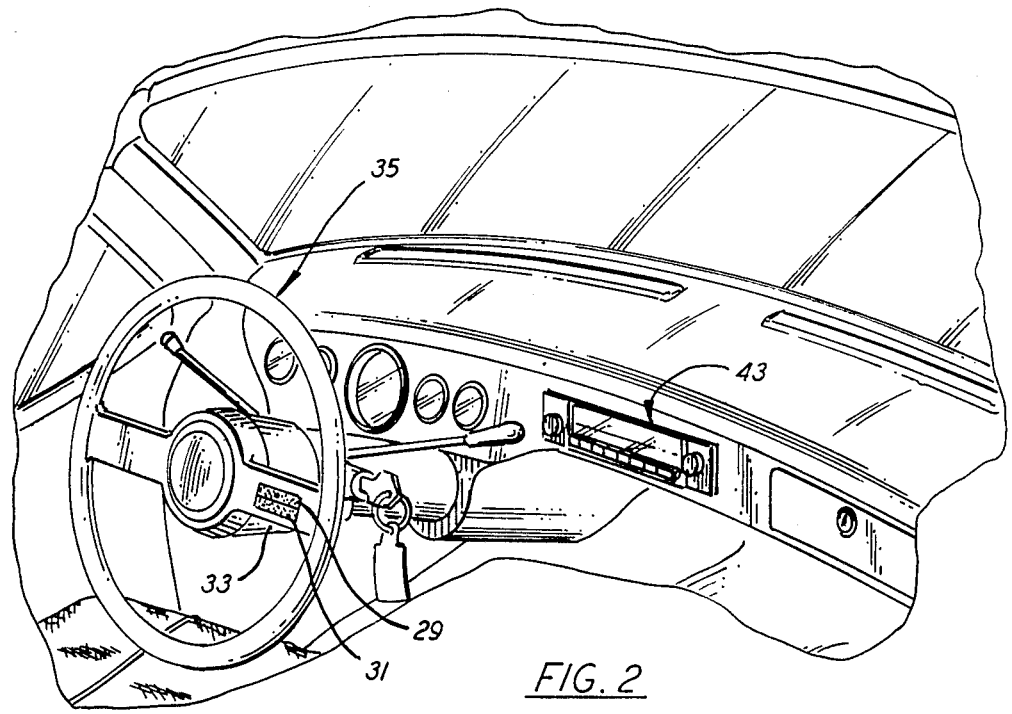
FIG. 2 is a perspective view of the control panel of a motor vehicle showing the steering wheel with sensors located in the steering wheel.
Figure 3:
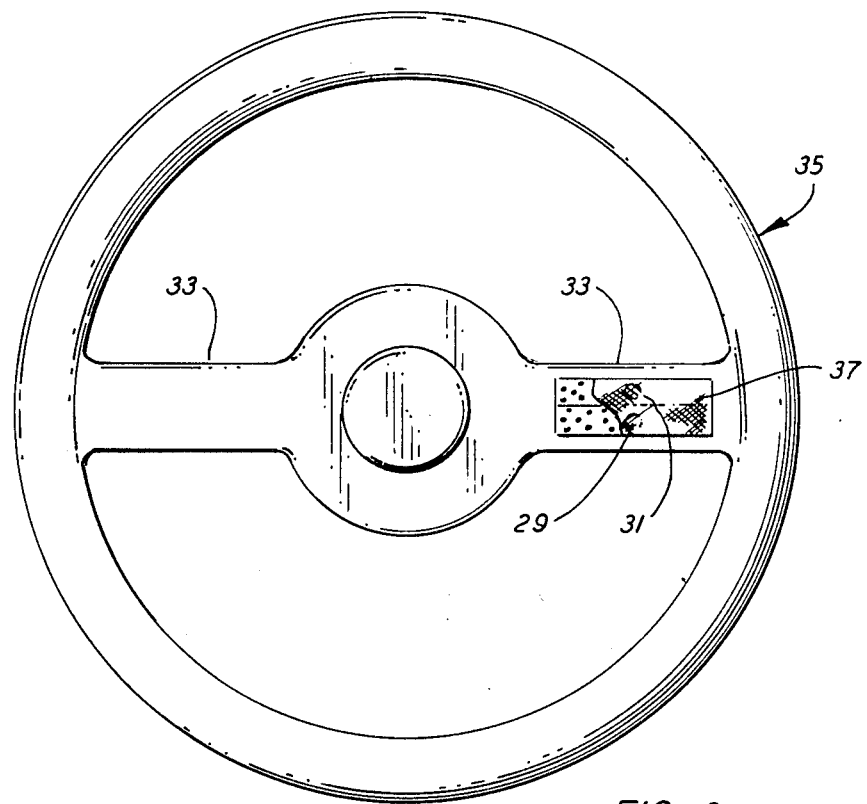
FIG. 3 is a plan view of a steering wheel for an automobile showing sensors located in the web of the steering wheel.

As best seen in FIG. 2, which portrays the invention utilized with a motor vehicle, an alcohol sensor 29 and proximity sensor 31 are located on the control panel 32 of the motor vehicle in a web 33 of the steering wheel 35. A screen 37 covers the sensors 29, 31 to prevent ready access to them. Preferably, the sensors 29, 31 are located in a web 33 which is horizontally oriented when the wheels of the automobile are in their forward position. The web 33 is made heavier and larger in order to provide space for the sensors 29, 31. All other equipment such as an amplifier 39 and power connector 41 can be located in any convenient location such as under the dashboard 43 or under the hood (not shown) of the automobile. Similar locations for the sensors 29, 31 can be found on any piece of equipment. Alcohol sensors 29 are well known including field sensors utilized by the police where the breath of one being tested entering the device causes a reading on a scale. Such scale reading is based upon an electrical impulse which according to this invention is amplified by the amplifier 30.

It is relatively apparent that an intoxicated driver, anxious to drive an automobile without being detected by the apparatus, would cover the alcohol sensor 29 in any available manner, as for example, by tape or by using cardboard to cover the alcohol sensor 29. It is for this reason that the proximity sensor 31 must also be included. Proximity sensors 31 are available in various types and are well known in the art to detect the presence of any object which blocks access to the proximity sensor 31 and therefore also would detect any obstruction of the access to the alcohol sensor 29. The proximity sensor 31, when actuated, produces the same result in the same manner as does the alcohol sensor 29.

The alcohol sensor 29 would in most circumstances require that the power convertor 41 convert and adjust the type and voltage of the power supplied by the machinery to that needed by both the alcohol sensor 29 and the proximity sensor 31. As for example, from 12 volt direct current to 24 volt alternating current. Therefore, the power convertor 41 is supplied electrical power from the battery 13 through leads 45. Power from the power convertor 41 is supplied to the proximity sensor 31 and the alcohol sensor 29 through leads 47. Power to the amplifier 39 is supplied from the power converter 41 through leads 49.

Both the alcohol sensor 29 and the proximity sensor 31 when activated, supply an electrical impulse. As best seen in FIG. 1, in the case of the alcohol sensor such electrical impulse would be supplied by a pair of leads 51 to the amplifier 39. In the case of the proximity sensor 31, the electrical impulse would be supplied by another pair of leads 53 to the amplifier 39. The amplifier 39, which is also readily available, amplifies the amount of the impulse. The amplified impulse from the alcohol sensor 29 is supplied to an alcohol sensor relay 55 and, in the case of the proximity sensor 31, to a proximity sensor relay 57. It would be possible, as an alternate, to have either one or both sensors 29, 31 activate only one relay.

Actuation of the alcohol sensor relay 55 closes an alcohol sensor contact 59, which is normally-open and is located in the starting circuit 11 which activates the two-pole solenoid 17. Similarly, the proximity sensor relay 57 closes a proximity sensor contact 61 which is normally-open and is also located in the starting circuit 11 in parallel with the alcohol sensor contact 59. In this way, should either access to the alcohol sensor 29 be blocked or the alcohol sensor 29 be activated, it would be impossible to close the contacts 18 of the two-pole solenoid 17 thereby totally preventing operation of the machinery such as a motor vehicle. The same concept would be used with any type of machinery, as for example even a large production tool, by placing the contacts 55, 57 in the circuit necessary to power the machinery.

While a preferred embodiment has been shown and described, various modifications and substitutions may be made without departing from the spirit and scope of this invention. Accordingly, it is understood that this invention has been described by way of illustration rather than limitation.

I claim:

1. An apparatus for preventing the operation of machinery, such as a motor vehicle, by an intoxicated operator, the machinery having a control panel where the operator is situated when operating the machinery and having an electrical power source for actuating the machinery, such apparatus comprising:

an alcohol sensor located in the vicinity of said control panel, said alcohol sensor including means for detecting the state of intoxication of the operator from the operator's breath and a proximity sensor to detect any object obstructing access to the alcohol sensor, said alcohol sensor and said proximity sensor being connected to the power source of the machinery;

an amplifier connected to said alcohol sensor and to said proximity sensor, said alcohol sensor being adapted to transmit an alcohol sensor electrical impulse when activated and said proximity sensor being adapted to transmit a proximity sensor electrical impulse when activated, said alcohol sensor being electrically connected to said amplifier to transmit the alcohol sensor electrical impulse to said amplifier, said proximity sensor being electrically connected to said amplifier to transmit the proximity sensor electrical impulse to said amplifier, said amplifier being connected to the power source;

an alcohol sensor relay and a proximity sensor relay, each relay being connected to said amplifier, said alcohol sensor relay being actuated by said alcohol sensor through said amplifier and said proximity sensor relay being actuated by said proximity sensor through said amplifier, said alcohol sensor relay including an alcohol sensor contact and said proximity sensor relay including a proximity sensor contact, said alcohol sensor contact and said proximity sensor contact each being normally open and being connected in parallel with one another;

a power converting means for converting direct current to alternating current, said power source being connected to said alcohol sensor and said proximity sensor and to said amplifier through said power converting means; and an electrical circuit opening means which is normally closed and which is electrically connected in series with said power source, said alcohol sensor contact and said proximity sensor contact being electrically connected to said electrical circuit opening means, said electrical circuit opening means being opened when said alcohol relay is energized, said electrical circuit opening means being opened when said proximity relay is energized.

2. An apparatus according to claim 1 wherein said electrical circuit opening means is a two pole solenoid having a coil with an energizing circuit, said alcohol sensor relay and said proximity sensor contact being located in such energizing circuit.

* * * * *